US011331083B2

(12) United States Patent
Lee et al.

(10) Patent No.: US 11,331,083 B2
(45) Date of Patent: May 17, 2022

(54) ULTRASOUND DIAGNOSIS APPARATUS AND METHOD OF OPERATING THE SAME

(71) Applicant: SAMSUNG MEDISON CO., LTD., Hongcheon-gun (KR)

(72) Inventors: Sang-mok Lee, Seongnam-si (KR); Yong-cheol Hyeon, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 749 days.

(21) Appl. No.: 16/159,127

(22) Filed: Oct. 12, 2018

(65) Prior Publication Data

US 2019/0110777 A1 Apr. 18, 2019

Related U.S. Application Data

(60) Provisional application No. 62/572,676, filed on Oct. 16, 2017.

(30) Foreign Application Priority Data

Apr. 4, 2018 (KR) .................. 10-2018-0039331

(51) Int. Cl.
*A61B 8/00* (2006.01)
*A61B 8/08* (2006.01)
*G01S 7/52* (2006.01)

(52) U.S. Cl.
CPC .............. *A61B 8/56* (2013.01); *A61B 8/4405* (2013.01); *A61B 8/485* (2013.01); *A61B 8/5246* (2013.01);
(Continued)

(58) Field of Classification Search
CPC ......... A61B 8/56; A61B 8/4405; A61B 8/485; A61B 8/5246; A61B 8/54
See application file for complete search history.

(56) References Cited

U.S. PATENT DOCUMENTS 9,101,958 B2   8/2015 Kandori et al.
2004/0210134 A1   10/2004 Hynynen et al.
(Continued)

FOREIGN PATENT DOCUMENTS

JP   2011-120794 A   6/2011
JP   2015-58251 A   3/2015
KR   10-2017-0059672 A   5/2017

OTHER PUBLICATIONS

Communication dated Feb. 21, 2019, issued by the European Patent Office in counterpart European Application No. 18200229.5.

*Primary Examiner* — Joel F Brutus
(74) *Attorney, Agent, or Firm* — Sughrue Mion, PLLC

(57) ABSTRACT

An ultrasound diagnosis apparatus includes: a high voltage power source; a transmission circuit to receive power from the high voltage power source, generate a pulse generating an ultrasound wave, and apply the ultrasound wave to a probe in the ultrasound diagnosis apparatus; a power circuit to receive the power from the high voltage power source and charge a capacitor with electric energy when the ultrasound diagnosis apparatus operates in a shear wave mode, and supply, to the transmission circuit, shear wave mode power used for generating a shear wave, based on the electric energy; and a processor to control the power circuit to supply the shear wave mode power when the shear wave mode is in operation, and control the high voltage power source and the power circuit such that insufficient power of the shear wave mode power is supplied from the high voltage power source to the transmission circuit.

20 Claims, 13 Drawing Sheets

(52) U.S. Cl.
CPC .............. *A61B 8/54* (2013.01); *G01S 7/5202* (2013.01); *G01S 7/52042* (2013.01); *G01S 7/52096* (2013.01); *G01S 7/52019* (2013.01)

(56) References Cited

U.S. PATENT DOCUMENTS

| | | | |
|---|---|---|---|
| 2009/0206676 A1* | 8/2009 | Chu ...................... | B06B 1/0215 |
| | | | 307/106 |
| 2012/0197130 A1* | 8/2012 | Amemiya .............. | G01S 7/5208 |
| | | | 600/459 |
| 2012/0200196 A1 | 8/2012 | Amemiya | |
| 2014/0074076 A1 | 3/2014 | Gertner | |
| 2015/0148672 A1* | 5/2015 | Savord .................. | B06B 1/0215 |
| | | | 600/438 |
| 2015/0209013 A1 | 7/2015 | Tsymbalenko | |
| 2016/0095582 A1 | 4/2016 | Iwama et al. | |
| 2016/0128674 A1 | 5/2016 | Shin et al. | |
| 2016/0249883 A1* | 9/2016 | Lee ....................... | A61B 8/4472 |
| | | | 600/438 |
| 2016/0270764 A1 | 9/2016 | Wodecki | |
| 2016/0374645 A1* | 12/2016 | Kim ....................... | G01S 7/5202 |
| | | | 600/447 |
| 2017/0014104 A1 | 1/2017 | Yamakoshi | |
| 2017/0276651 A1 | 9/2017 | Hall | |

\* cited by examiner ial Application No. 62/572, 676, filed on Oct. 16, 2017, in the US Patent and Trademark Office and to Korean Patent Application No. 10-2018-0039331, filed on Apr. 4, 2018, in the Korean Intellectual Property Office, the disclosures of which are incorporated by reference herein in their entirety.

BACKGROUND

1. Field

The disclosure relates to ultrasound diagnosis apparatuses and methods of operating the same.

2. Description of Related Art

Ultrasound diagnosis apparatuses transmit, to an object, ultrasound signals generated by transducers of a probe and detect information about signals reflected from the object, thereby obtaining at least one image of an internal part, for example, soft tissue or blood flow, of the object.

SUMMARY

An ultrasound diagnosis apparatus may control a power circuit which reduces a load of a high voltage power source during a shear wave mode and may supply power required for generating a shear wave to a transmission circuit, thereby generating a distortion-free pulse.

A power circuit may be designed in a board form and mounted on an ultrasound diagnosis apparatus without the power circuit.

Provided is a non-transitory computer-readable recording medium having recorded thereon a program for executing, on a computer, methods of operating the ultrasound diagnosis apparatus.

Additional aspects will be set forth in part in the description which follows and, in part, will be apparent from the description, or may be learned by practice of the presented embodiments.

In accordance with an aspect of the disclosure, an ultrasound diagnosis apparatus includes: a high voltage power source; a transmission circuit configured to receive power from the high voltage power source, generate a pulse generating an ultrasound wave, and apply the ultrasound wave to a probe in the ultrasound diagnosis apparatus; a power circuit configured to receive the power from the high voltage power source and charge a capacitor with electric energy when the ultrasound diagnosis apparatus operates in a shear wave mode, and supply, to the transmission circuit, shear wave mode power used for generating a shear wave based on the electric energy; and a processor configured to control the power circuit configured to supply the shear wave mode power when the shear wave mode is in operation, and control the high voltage power source and the power circuit such that insufficient power of the shear wave mode power is supplied from the high voltage power source to the transmission circuit.

When the electric energy stored in the power circuit is reduced when the shear wave mode power is supplied from the power circuit to the transmission circuit, the processor may be further configured to control the high voltage power source and the power circuit such that the insufficient power supplied from the high voltage power source increases and the shear wave mode power is supplied constantly from the power circuit to the transmission circuit.

The power circuit may include: a capacitor to charge the electric energy for supplying the shear wave mode power; a constant current circuit connected with the high voltage power source, and configured to supply the electric energy for supplying the shear wave mode power to the capacitor; a first switch configured to control connection between the constant current circuit and the capacitor; and a second switch configured to control connection between the capacitor and the transmission circuit.

The processor may be further configured to control the power circuit such that the connection between the constant current circuit and the capacitor is cut off by turning off the first switch, and the capacitor is connected with the transmission circuit by turning on the second switch, to supply the shear wave mode power to the transmission circuit based on the electric energy stored in the capacitor.

The processor may be further configured to control the power circuit such that the constant current circuit is connected with the capacitor by turning on the first switch, and the connection between the capacitor and the transmission circuit is cut off by turning off the second switch, to charge the capacitor with the electric energy based on a current supplied from the constant current circuit.

The power circuit may further include a discharging circuit configured to discharge the electric energy stored in the capacitor.

The discharging circuit may include a third switch configured to control connection between the capacitor and a ground, and when the shear wave mode ends or an operation of charging the capacitor with the electric energy is not performed, the processor may be further configured to control the discharging circuit such that the capacitor is connected with the ground by turning on the third switch to discharge the electric energy stored in the capacitor.

The transmission circuit may be further configured to generate a pulse generating the shear wave by using the shear wave mode power and apply the pulse to the probe.

The processor may be further configured to control the probe such that the shear wave is transmitted to an object, an echo signal of the shear wave, reflected from the object, is received to calculate a propagation velocity of the shear wave, and an elasticity image is generated.

The processor may be further configured to control the power circuit such that the electric energy stored in the power circuit is supplied to the transmission circuit when the shear wave mode is in operation, and control the power circuit such that the electric energy stored in the power circuit is not supplied to the transmission circuit when a mode other than the shear wave mode is in operation.

In accordance with another aspect of the disclosure, a method of operating an ultrasound diagnosis apparatus for generating a shear wave includes: controlling a power circuit in the ultrasound diagnosis apparatus such that power supplied from a high voltage power source in the ultrasound diagnosis apparatus is stored in a capacitor as electric energy when the ultrasound diagnosis apparatus operates in a shear wave mode, and shear wave mode power used for generating the shear wave is supplied to a transmission circuit in the ultrasound diagnosis apparatus, based on the electric energy; controlling the high voltage power source such that insufficient power of the shear wave mode power is supplied to the transmission circuit when the shear wave mode is in operation; and controlling the transmission circuit to generate a pulse for generating the shear wave by using the shear wave mode power, and apply the pulse to a probe in the ultrasound diagnosis apparatus.

In accordance with another aspect of the disclosure, a non-transitory computer-readable recording medium having recorded thereon a program for executing a method of operating an ultrasound diagnosis apparatus for generating a shear wave is provided, the method including: controlling a power circuit in the ultrasound diagnosis apparatus such that power supplied from a high voltage power source in the ultrasound diagnosis apparatus is stored as electric energy when the ultrasound diagnosis apparatus operates in a shear wave mode, and shear wave mode power used for generating the shear wave is supplied to a transmission circuit in the ultrasound diagnosis apparatus, based on the electric energy; controlling the high voltage power source such that insufficient power of the shear wave mode power is supplied to the transmission circuit when the shear wave mode is in operation; and controlling the transmission circuit to generate a pulse for generating the shear wave by using the shear wave mode power, and apply the pulse to a probe in the ultrasound diagnosis apparatus.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1:
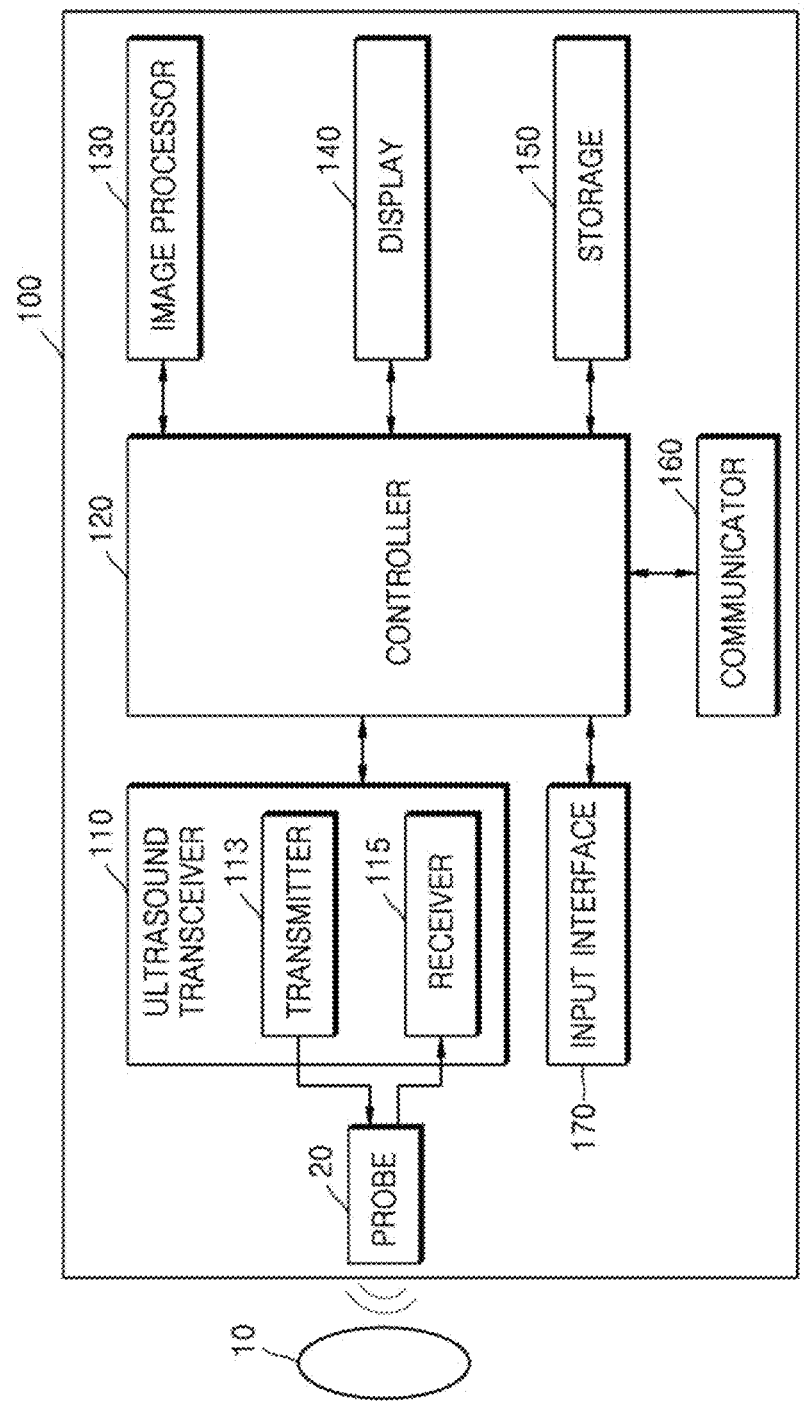
FIG. 1 is a block diagram of an ultrasound diagnosis apparatus according to an embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of the exemplary embodiments. Thus, it is apparent that the exemplary embodiments can be carried out without those specifically defined matters. Also, well-known functions or constructions are not described in detail since they would obscure the exemplary embodiments with unnecessary detail.

Terms such as "part" and "portion" used herein denote those that may be embodied by software or hardware. According to the exemplary embodiments, a plurality of parts or portions may be embodied by a single unit or element, or a single part or portion may include a plurality of elements.

In the exemplary embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom.

Throughout the specification, an ultrasound image refers to an image of an object processed based on ultrasound signals transmitted to the object and reflected therefrom.

FIG. 1 is a block diagram illustrating a configuration of an ultrasound diagnosis apparatus 100, i.e., a diagnosis apparatus, according to an exemplary embodiment.

Referring to FIG. 1, the ultrasound diagnosis apparatus 100 may include a probe 20, an ultrasound transceiver 110, a controller 120, an image processor 130, one or more displays 140, a storage 150, e.g., a memory, a communicator 160, i.e., a communication device or an interface, and an input interface 170.

The ultrasound diagnosis apparatus 100 may be of a cart-type or a portable-type ultrasound diagnosis apparatus, that is portable, moveable, mobile, or hand-held. Examples of the portable-type ultrasound diagnosis apparatus 100 may include a smart phone, a laptop computer, a personal digital assistant (PDA), and a tablet personal computer (PC), each of which may include a probe and a software application, but embodiments are not limited thereto.

The probe 20 may include a plurality of transducers. The plurality of transducers may transmit ultrasound signals to an object 10 in response to transmitting signals received by the probe 20, from a transmitter 113. The plurality of transducers may receive ultrasound signals reflected from the object 10 to generate reception signals. In addition, the probe 20 and the ultrasound diagnosis apparatus 100 may be formed in one body (e.g., arranged in a single housing), or the probe 20 and the ultrasound diagnosis apparatus 100 may be formed separately (e.g., arranged separately in separate housings) but linked wirelessly or via wires. In addition, the ultrasound diagnosis apparatus 100 may include one or more probes 20 according to embodiments.

The controller 120 may control the transmitter 113 to generate transmission signals to be applied to each of the plurality of transducers based on a position and a focal point of the plurality of transducers included in the probe 20.

The controller 120 may control the ultrasound receiver 115 to generate ultrasound data by converting reception signals received from the probe 20 from analog to digital signals and summing the reception signals converted into digital form, based on a position and a focal point of the plurality of transducers.

The image processor 130 may generate an ultrasound image by using ultrasound data generated by the ultrasound receiver 115.

The display 140 may display a generated ultrasound image and various pieces of information processed by the ultrasound diagnosis apparatus 100. The ultrasound diagnosis apparatus 100 may include two or more displays 140 according to the present exemplary embodiment. The display 140 may include a touch screen in combination with a touch panel.

The controller 120 may control the operations of the ultrasound diagnosis apparatus 100 and a flow of signals between the internal elements of the ultrasound diagnosis apparatus 100. The controller 120 may include a memory for storing a program or data to perform functions of the ultrasound diagnosis apparatus 100 and a processor and/or a microprocessor (not shown) for processing the program or data. For example, the controller 120 may control the operation of the ultrasound diagnosis apparatus 100 by receiving a control signal from the input interface 170 or an external apparatus.

The ultrasound diagnosis apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the controller 120 so that the controller 120 may control the ultrasound diagnosis apparatus 100 in response to the received control signal.

The controller 120 may transmit a control signal to the external apparatus via the communicator 160 so that the external apparatus may be controlled in response to the control signal of the controller 120.

For example, the external apparatus connected to the ultrasound diagnosis apparatus 100 may process the data of the external apparatus in response to the control signal of the controller 120 received via the communicator 160.

A program for controlling the ultrasound diagnosis apparatus 100 may be installed in the external apparatus. The program may include instructions to perform some operations of the controller 120 or all of the operations of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound diagnosis apparatus 100, input and/or output ultrasound data, ultrasound images, applications, etc.

The input interface 170 may receive a user's input to control the ultrasound diagnosis apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an exemplary embodiment is not limited thereto.

An example of the ultrasound diagnosis apparatus 100 according to the present exemplary embodiment is described below with reference to FIGS. 2A, 2B, and 2C.

Figure 2C:
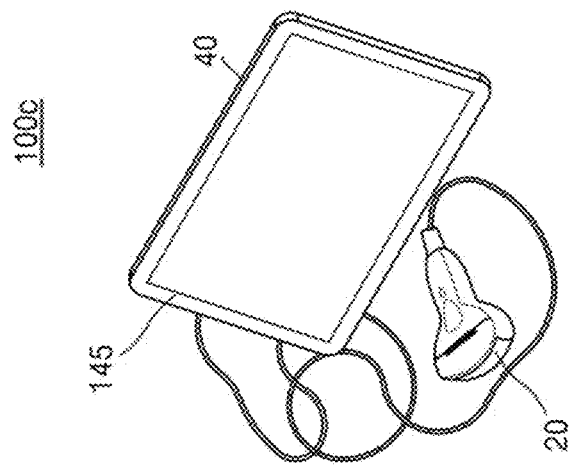
FIGS. 2A to 2C are views of an ultrasound diagnosis apparatus according to an embodiment.
Figure 2B:
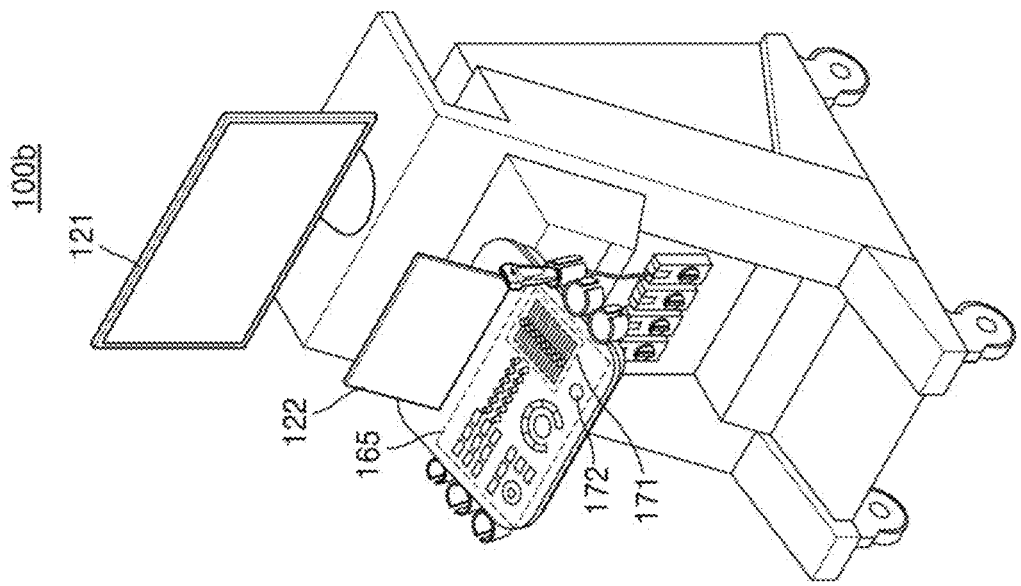
Figure 2A:
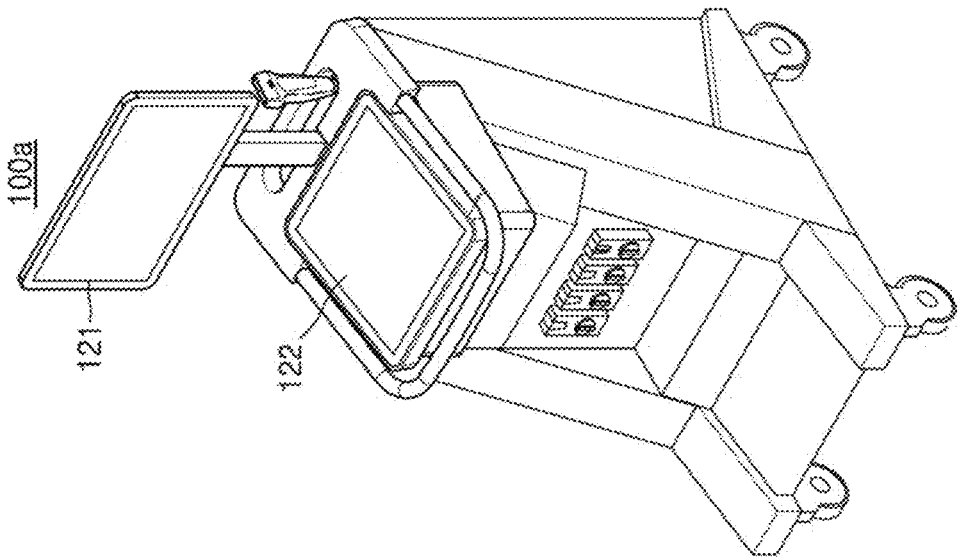

FIGS. 2A, 2B, and 2C are diagrams illustrating an ultrasound diagnosis apparatus 100 according to an exemplary embodiment.

Referring to FIGS. 2A and 2B, the ultrasound diagnosis apparatus 100 may include a main display 121 and a sub-display 122. At least one among the main display 121 and the sub-display 122 may include a touch screen. The main display 121 and the sub-display 122 may display ultrasound images and/or various information processed by the ultrasound diagnosis apparatus 100. The main display 121 and the sub-display 122 may provide graphical user interfaces (GUIs), thereby receiving user inputs of data to control the ultrasound diagnosis apparatus 100. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound diagnosis apparatus 100 may control the display of the ultrasound image on the main display 121 by using the input control data.

Referring to FIG. 2B, the ultrasound diagnosis apparatus 100 may include a control panel 165. The control panel 165 may include buttons, trackballs, jog switches, or knobs, and may receive data to control the ultrasound diagnosis apparatus 100 from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound diagnosis apparatus 100 may keep displaying a frame image at that time point.

The buttons, trackballs, jog switches, and knobs included in the control panel 165 may be provided as a GUI to the main display 121 or the sub-display 122.

Referring to FIG. 2C, the ultrasound diagnosis apparatus 100 may include a portable device. An example of the portable ultrasound diagnosis apparatus 100 may include, for example, smart phones including probes and applications, laptop computers, PDAs, or tablet PCs, but an exemplary embodiment is not limited thereto.

The ultrasound diagnosis apparatus 100 may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound diagnosis apparatus 100, and a GUI.

Figure 3:
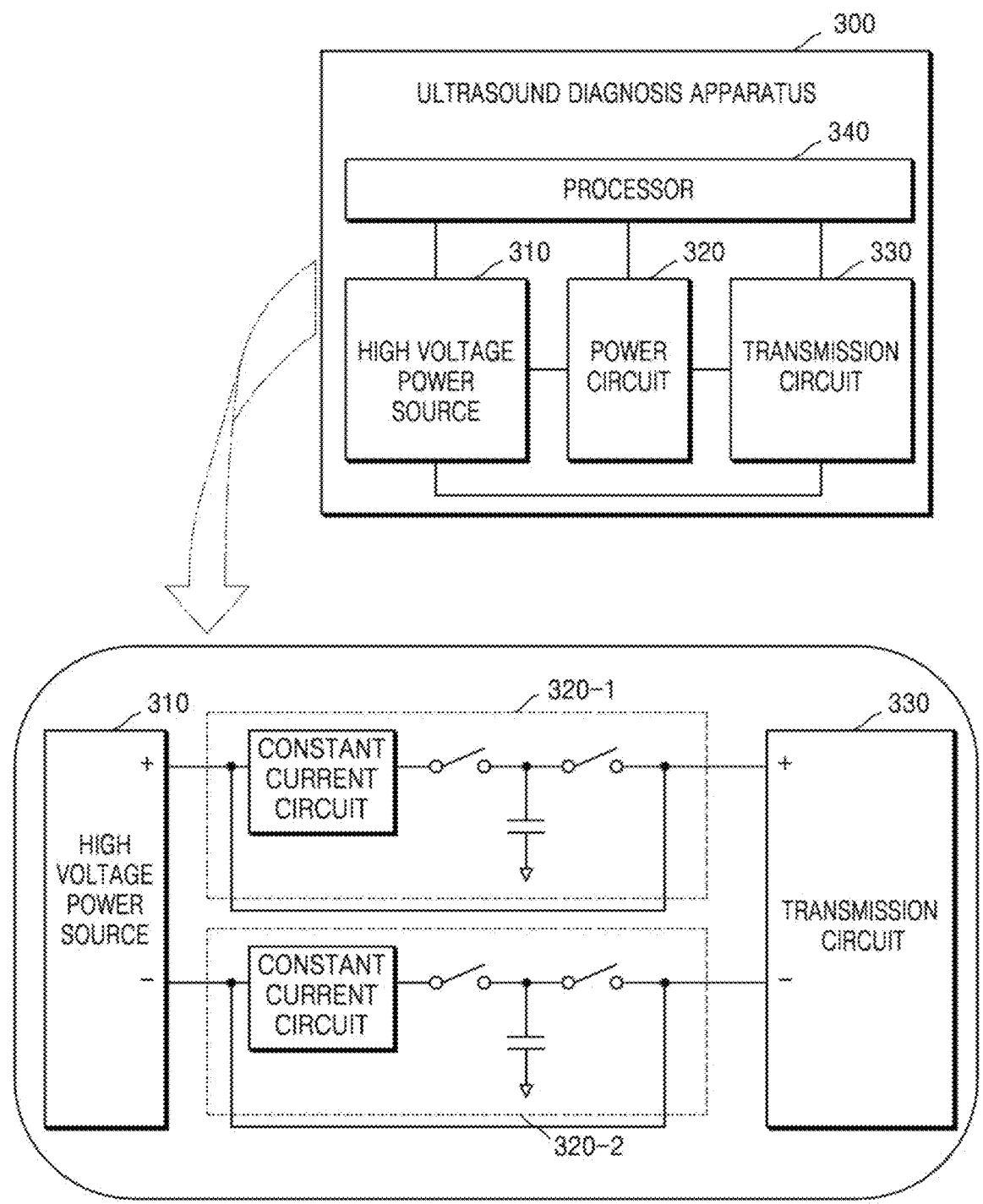
FIG. 3 is a block diagram of an ultrasound diagnosis apparatus according to an embodiment.

FIG. 3 is a block diagram of an ultrasound diagnosis apparatus 300 according to an embodiment.

The ultrasound diagnosis apparatus 300 may include a high voltage power source 310, a transmission circuit 330, a power circuit 320, and a processor 340. However, the ultrasound diagnosis apparatus 300 may include the number of elements less than the number of the shown elements, or may include the number of elements greater than the number of the shown elements. The ultrasound diagnosis apparatus 300 shown in FIG. 3 may equally correspond to the ultrasound diagnosis apparatus 100 shown in FIG. 1. The elements are described below.

The high voltage power source 310 may supply power to the power circuit 320 and the transmission circuit 330. When the ultrasound diagnosis apparatus 300 operates in a shear wave mode, the power circuit 320 may be charged with electric energy by receiving power from the high voltage power source 310. The power circuit 320 may supply shear wave mode power used for generating a shear wave to the transmission circuit 330 based on the electric energy. Also, the transmission circuit 330 may receive power from the high voltage power source 310, generate a pulse for generating an ultrasound wave, and apply the generated pulse to a probe (not shown) in the ultrasound diagnosis apparatus 300.

For example, the power circuit 320 may include a capacitor, a constant current circuit, a first switch, and a second switch. The capacitor may be charged with electric energy for supplying shear wave mode power. Here, one end of the capacitor may be connected with the high voltage power source 310, and the other end of the capacitor may be connected to a ground. The constant current circuit may be connected with the high voltage power source 310, and may supply electric energy for supplying shear wave mode power to the capacitor. The first switch may control connection between the constant current circuit and the capacitor. The second switch may control connection between the capacitor and the transmission circuit 330. Also, as illustrated in FIG. 3, a power circuit 320-1 may be connected and arranged between a (+) terminal of the high voltage power source 310 and a (+) terminal of the transmission circuit 330. Also, a power circuit 320-2 may be connected and arranged between a (−) terminal of the high voltage power source 310 and a (−) terminal of the transmission circuit 330.

When a shear wave mode is in operation, the processor 340 may control the power circuit 320 which supplies shear wave mode power. Also, the processor 340 may control the high voltage power source 310 such that the shear wave mode power is supplied from the high voltage power source 310 to the transmission circuit 330. For example, the processor 340 may control the high voltage power source 310 such that insufficient power of the shear wave mode power is supplied from the high voltage power source 310 to the transmission circuit 330.

When the power circuit 320 supplies the shear wave mode power to the transmission circuit 330, the electric energy stored in the capacitor in the power circuit 320 may be reduced. The processor 340 may control the power circuit 320 and the high voltage power source 310 such that insufficient power of the shear wave mode power supplied from the high voltage power source 310 increases. The processor 340 may allow insufficient power of the transverse mode power to be supplied to the transmission circuit 330 by controlling the high voltage power source 310 and the power circuit 320 such that a magnitude of the insufficient power of the shear wave mode power increases as much as a magnitude by which the shear wave mode power supplied from the power circuit 320 to the transmission circuit 330 is reduced. The processor 340 may control supplying of the shear wave mode power to fill electric energy reduced in the capacitor by controlling the power circuit 320 and the high voltage power source 310. That is, the processor 340 may control the power circuit 320 and the high voltage power source 310 such that the shear wave mode power is constantly supplied from the power circuit 320 to the transmission circuit 330.

The processor 340 may control the power circuit 320 such that the capacitor is charged with electric energy based on a current supplied from the constant current circuit. Specifically, the processor 340 may control the power circuit 320 such that the constant current circuit is connected with the capacitor by turning on the first switch and connection between the capacitor and the transmission circuit 330 is cut off by turning off the second switch. A process of controlling the power circuit 320 such that the capacitor in the power circuit 320 is charged with electric energy is described with reference to FIG. 4.

The processor 340 may control the power circuit 320 such that the shear wave mode power is supplied to the transmission circuit 330 based on the electric energy stored in the capacitor in the power circuit 320. Specifically, the processor 340 may control the power circuit 320 to cut off connection between the constant current circuit and the capacitor by turning off the first switch, and to connect the capacitor with the transmission circuit 330 by turning on the second switch. A process of controlling the power circuit 320 such that the shear wave mode power is supplied to the transmission circuit 330 by using the electric energy stored in the capacitor in the power circuit 320 is described with reference to FIG. 5.

Also, the power circuit 320 may further include a discharging circuit which discharges the electric energy stored in the capacitor in the power circuit 320. The discharging circuit may include a third switch controlling connection between the capacitor and a ground.

In the case where the shear wave mode ends or an operation of charging the capacitor with electric energy is not performed, the processor 340 may control the discharging circuit such that the capacitor is connected with the ground by turning on the third switch. That is, the processor may control the discharging circuit to discharge the electric energy stored in the capacitor. A process of discharging the electric energy stored in the capacitor in the power circuit 320 is described with reference to FIGS. 10 and 11.

The transmission circuit 330 may supply a driving signal to a probe (not shown), and include a pulse generator, a transmission delay, and a pulser. The pulse generator may generate a pulse for forming a transmission ultrasound wave corresponding to a predetermined pulse repetition frequency (PRF). The transmission delay may apply a delay time for determining transmission directionality to a pulse. Pulses to which a delay time has been applied may respectively correspond to a plurality of piezoelectric vibrators included in the probe (not shown). The pulser may apply a driving signal (or a driving pulse) to the probe (not shown) with a timing corresponding to each pulse to which the delay time has been applied. The transmission circuit 330 may generate a pulse generating a shear wave by using shear wave mode power. The transmission circuit 330 may apply the generated pulse to the probe (not shown). The processor 340 may control the probe (not shown) to transmit a shear wave to an object.

Also, the transmission circuit 330 may process an echo signal received from the probe (not shown) to generate ultrasound data, and include an amplifier, an analog digital converter (ADC), a reception delay, and a summer. The amplifier may amplify an echo signal for each channel, and the ADC may analog-digital convert an amplified echo signal. The reception delay may apply a delay time for determining reception directionality to a digital-converted echo signal, and the summer may generate ultrasound data by summing echo signals processed by the reception delay. The transmission circuit 330 may receive an echo signal of a shear wave reflected from an object to obtain ultrasound data of the object. The processor 340 may calculate a propagation velocity of a shear wave by using ultrasound data obtained by receiving an echo signal of the shear wave reflected from the object, and generate an elasticity image based on the calculated propagation velocity.

Meanwhile, when the ultrasound diagnosis apparatus 300 operates in a shear wave mode, the processor 340 may control the power circuit 320 such that electric energy stored in the power circuit 320 is supplied to the transmission circuit 330. Meanwhile, when the ultrasound diagnosis apparatus 300 operates in a mode other than the shear wave mode, the processor 340 may control the power circuit 320 such that electric energy stored in the power circuit 320 is not supplied to the transmission circuit 330.

The ultrasound diagnosis apparatus 300 may further include a memory (not shown). The memory (not shown) may store software or a computer program related to a method of operating the ultrasound diagnosis apparatus 300. For example, the memory (not shown) may include instructions of controlling the high voltage power source 310, the power circuit 320, and the transmission circuit 330 in the ultrasound diagnosis apparatus 300 to generate a shear wave.

Specifically, for example, the instructions may include an instruction of controlling the power circuit 320 such that power supplied from the high voltage power source 310 is stored as electric energy and shear wave mode power is supplied to the transmission circuit 330 based on the electric energy when the ultrasound diagnosis apparatus 300 operates in a shear wave mode, an instruction of controlling the high voltage power source 310 such that insufficient power of the shear wave mode power is supplied to the transmission circuit 330 when the shear wave mode is in operation, and an instruction of controlling the transmission circuit 330 to generate a pulse for generating a shear wave by using shear wave mode power, and apply the pulse to the probe (not shown) in the ultrasound diagnosis apparatus 300. The processor 340 may control an operation of the ultrasound diagnosis apparatus 300 by executing the instructions stored in the memory (not shown).

The ultrasound diagnosis apparatus 300 may include a central operation processor to generally control operations of the high voltage power source 310, the power circuit 320, the transmission circuit 330, and the processor 340. The central operation processor may include an array of a plurality of logic gates, or include a combination of a general purpose microprocessor and a memory in which a program executable by the microprocessor is stored. Also, it will be understood by those of ordinary skill in the art that the central operation processor may be implemented as another type of hardware.

Meanwhile, operations of the high voltage power source 310, the power circuit 320, the transmission circuit 330, and the processor 340 of the ultrasound diagnosis apparatus 300 may be implemented as a computer-readable recording medium which stores an instruction or data executable by a computer or a processor. The operations may be writable as a program executable on a computer, and may be implemented by a general-purpose digital computer which operates such a program by using a computer-readable recording medium. The computer-readable recording medium may include a read-only memory (ROM), a random-access memory (RAM), a flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, DVD-ROMs, BD-ROMs, BD-Rs, BD-R LTHs, BD-REs, a magnetic tape, a floppy disk, an optical magnetic data storage, an optical data storage, a hard disk, a solid-state disk (SSD), and any device which may store an instruction or software, related data, a data file, and data structures and may provide the instruction or software, the related data, the data file, and the data structures to a processor or a computer such that the processor or the computer executes the instruction.

Hereinafter, various operations or applications performed by the ultrasound diagnosis apparatus 300 are described. Content which may be clearly understood and expected by those of ordinary skill in the art may be understood as general implementation even though any configuration among the high voltage power source 310, the power circuit 320, the transmission circuit 330, and the processor 340 is not specified, and the scope of the present disclosure is not limited by a title or physical/logical structure of a specific configuration.

Figure 4:
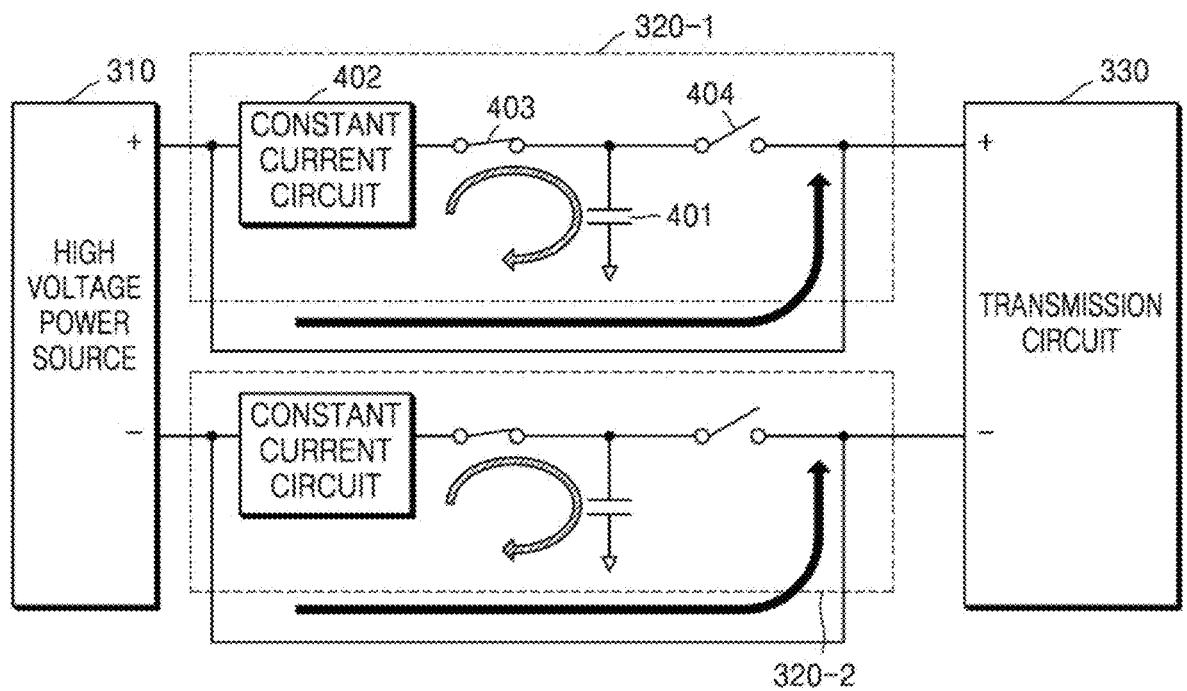
FIG. 4 is a view for explaining a process of controlling a power circuit such that a capacitor in the power circuit is charged with electric energy for supplying shear wave mode power to a transmission circuit in an ultrasound diagnosis apparatus, according to an embodiment.

FIG. 4 is a view for explaining a process of controlling a power circuit such that a capacitor in the power circuit is charged with electric energy for supplying shear wave mode power to a transmission circuit in an ultrasound diagnosis apparatus according to an embodiment.

Referring to FIG. 4, the power circuit 320 may include a capacitor 401, a constant current circuit 402, a first switch 403, and a second switch 404. It will be understood by those of ordinary skill in the art that the power circuit 320 may include other elements besides the elements shown in FIG. 4.

Meanwhile, when the ultrasound diagnosis apparatus 300 operates in a shear wave mode, the ultrasound diagnosis apparatus 300 may charge the power circuit 320 with electric energy to supply shear wave mode power to the transmission circuit 330. In this case, since an overload may be generated to the high voltage power source 310 when the capacitor 401 is charged with electric energy fast, the power circuit 320 may charge the capacitor 401 with the electric energy by using the constant current circuit 402. The constant current circuit 402 is a circuit through which a constant current flows regardless of a value of a voltage applied to both ends of the constant current circuit 402. Though a detailed configuration view of the constant current circuit 402 is not provided in FIG. 4, the constant current circuit 402 may include a predetermined transistor.

As illustrated in FIG. 4, the capacitor 401 may be charged with electric energy for supplying shear wave mode power. Here, one side of the capacitor 401 may be connected with the high voltage power source 310, and another side of the capacitor 401 may be connected with the ground. The constant current circuit 402 may be connected with the high voltage power source 310 and may supply electric energy for supplying shear wave mode power. The first switch 403 may control connection between the constant current circuit 402 and the capacitor 401. The second switch 404 may control connection between the capacitor 401 and the transmission circuit 330.

Also, as illustrated in FIG. 4, the power circuit 320-1 may be connected and arranged between the (+) terminal of the high voltage power source 310 and the (+) terminal of the transmission circuit 330. Also, the power circuit 320-2 may be connected and arranged between the (−) terminal of the high voltage power source 310 and the (−) terminal of the transmission circuit 330.

The power circuit 320 may connect the constant current circuit 402 with the capacitor 401 by turning on the first switch 403, and cut off connection between the capacitor 401 and the transmission circuit 330 by turning off the second switch 404. The capacitor 401 may be charged with electric energy based on a current supplied from the constant current circuit 402. Specifically, when a shear wave mode of the ultrasound diagnosis apparatus 300 is in operation, the high voltage power source 310 may supply electric energy to the capacitor 401 through the constant current circuit 402 in the power circuit 320. The power circuit 320 may charge the capacitor 401 with charge quantity based on a current supplied from the constant current circuit 402. In this case, the capacitor 401 may be charged with charge quantity in proportion to a capacity of the capacitor 401. Meanwhile, though one capacitor 401 is shown in FIG. 4, the capacitor 401 may be represented as an equivalent capacitor 401 including a plurality of capacitors.

Also, while the capacitor 401 is charged with electric energy, the high voltage power source 310 may supply power to the transmission circuit 330. Specifically, while the capacitor 401 is charged with the electric energy, as illustrated in FIG. 4, since the (+) terminal of the transmission circuit 330 may be connected with the (+) terminal of the high voltage power source 310, and the (−) terminal of the transmission circuit 330 may be connected with the (−) terminal of the high voltage power source 310, the high voltage power source 310 may supply power required by the transmission circuit 330 to the transmission circuit 330.

Figure 5:
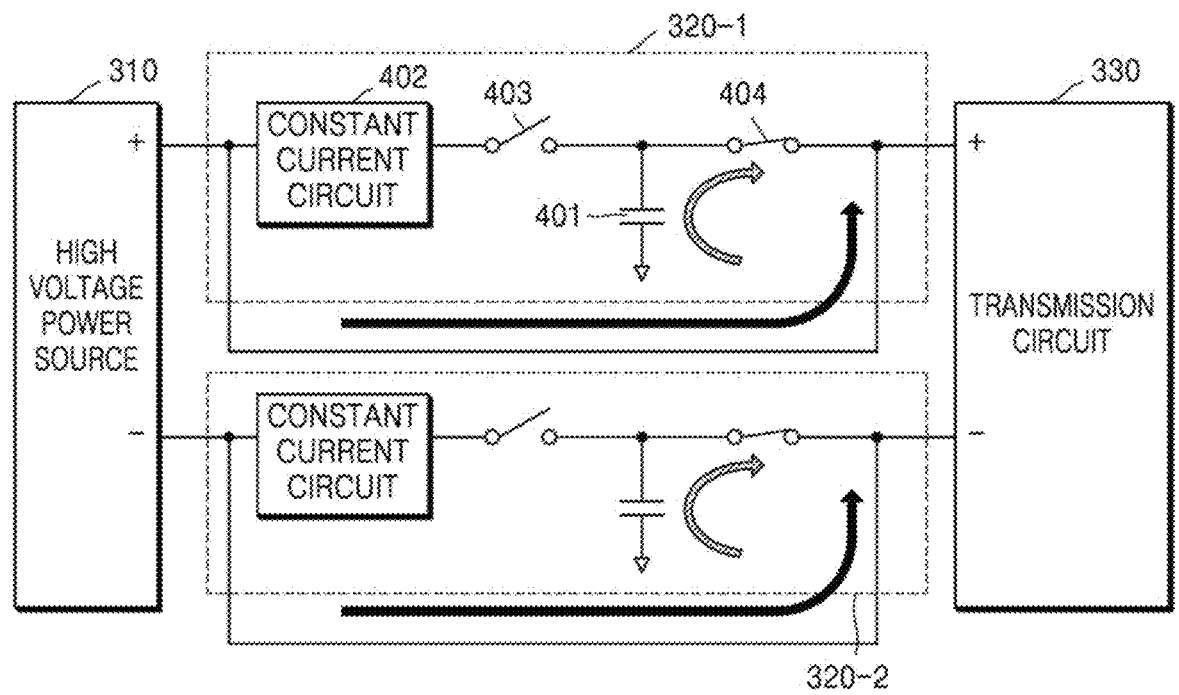
FIG. 5 is a view for explaining a process of controlling a power circuit such that shear wave mode power is supplied to a transmission circuit in the power circuit by using electric energy stored in a capacitor in the power circuit in an ultrasound diagnosis apparatus, according to an embodiment.

FIG. 5 is a view for explaining a process of controlling a power circuit such that shear wave mode power is supplied to a transmission circuit by using electric energy stored in a capacitor in the power circuit in an ultrasound diagnosis apparatus according to an embodiment.

When the capacitor 401 in the power circuit 320 is fully charged with electric energy, the power circuit 320 may supply shear wave mode power used for generating a shear wave to the transmission circuit 330 based on the electric energy stored in the capacitor 401. That is, the power circuit 320 may control the elements in the power circuit 320 such that an operation of the power circuit 320 is changed from an electric energy charging operation to a shear wave mode power supplying operation.

Specifically, as illustrated in FIG. 5, the power circuit 320 may cut off connection between the constant current circuit 402 and the capacitor 401 by turning off the first switch 403, and connect the capacitor 401 with the transmission circuit 330 by turning on the second switch 404. The power circuit 320 may supply shear wave mode power to the transmission circuit 330 based on the electric energy stored in the capacitor 401 depending on an operation control of the first switch 403 and the second switch 404.

When the ultrasound diagnosis apparatus 300 operates in the shear wave mode, since electric energy with which the capacitor 401 is charged is sufficient while shear wave mode power is initially supplied to the transmission circuit 330, the transmission circuit 330 may generate a distortion-free pulse by using only the shear wave mode power supplied from the power circuit 320. However, as the time elapses, since the electric energy with which the capacitor 401 is charged is reduced, and power supplied per unit time from the power circuit 320 to the transmission circuit 330 is reduced, the transmission circuit 330 cannot generate a distortion-free pulse by using only the shear wave mode power supplied from the power circuit 320. Therefore, when the electric energy with which the capacitor 401 is charged is reduced, the high voltage power source 310 may be controlled such that power is additionally supplied to the transmission circuit 330 as much as a reduced amount of the power supplied per unit time.

That is, when the power circuit 320 performs an operation of supplying shear wave mode power to the transmission circuit 330, the power circuit 320 may supply shear wave mode power to the transmission circuit 330 based on the electric energy with which the capacitor 401 is charged. Also, as the time elapses, when power per unit time supplied from the power circuit 320 to the transmission circuit 330 is reduced, the high voltage power source 310 may be controlled to supply insufficient power of the shear wave mode power to the transmission circuit 330 based on the electric energy with which the capacitor is charged. For example, the high voltage power source 310 may supply insufficient power of the shear wave mode power to the capacitor 401 in the power circuit 320 to complement the reduced energy of the capacitor 401. The power circuit 320 may be controlled such that the shear wave mode power is constantly supplied from the power circuit 320 to the transmission circuit 330 based on the complemented electric energy.

The ultrasound diagnosis apparatus 300 may control operations of the power circuit 320 and the high voltage power source 310 such that shear wave mode power is constantly supplied from the power circuit 320 to the transmission circuit 330.

Also, when the shear wave mode power is supplied to the transmission circuit 330 from the power circuit 320 and the high voltage power source 310, the capacitor 401 of a less capacity may be used than a case where the shear wave mode power is supplied from only the power circuit 320 or the high voltage power source 310. When the capacitor 401 of a less capacity is used, since a volume or an area, etc. occupied by the capacitor 401 is reduced, a volume or an area of the power circuit 320 may be reduced.

Figure 6:
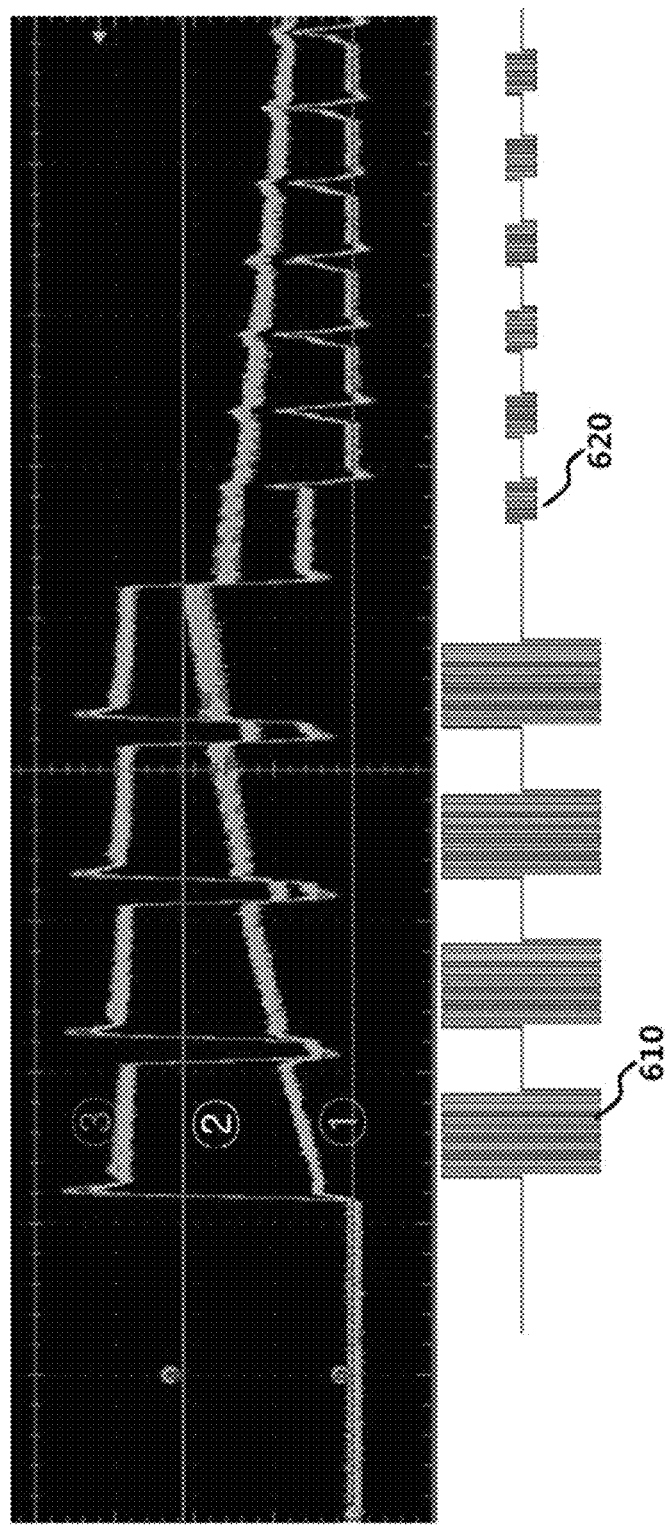
FIG. 6 is a view for explaining shear wave mode power supplied to a transmission circuit when an ultrasound diagnosis apparatus operates in a shear wave mode, according to an embodiment.

FIG. 6 is a view for explaining shear wave mode power supplied to the transmission circuit 330 when an ultrasound diagnosis apparatus operates in a shear wave mode according to an embodiment.

When the shear wave mode power is supplied from the power circuit 320 to the transmission circuit 330, electric energy with which the power circuit 320 is charged may be reduced. When the electric energy with which the power circuit 320 is charged is reduced, the power circuit 320 may not supply the shear wave mode power to the transmission circuit 330 constantly. That is, when a predetermined time elapses, since shear wave mode power that may be supplied from the power circuit 320 per unit time is gradually reduced, the ultrasound diagnosis apparatus 300 may control the power circuit 320 and the high voltage power source 310 such that the high voltage power source 310 supplies insufficient power that cannot be supplied to the transmission circuit 330 from the power circuit 320. Specifically, when electric energy with which the capacitor is charged is consumed and thus the stored electric energy is reduced, impedance of the capacitor may increase. When the impedance of the capacitor increases, electric energy supplied from the high voltage power source 310 to the power circuit 320 may be reduced. Therefore, the ultrasound diagnosis apparatus 300 may control the high voltage power source 310 and the power circuit 320 such that the high voltage power source 310 supplies insufficient power of the shear wave mode power from the high voltage power source 310 to the transmission circuit 330 as much as insufficient power of the shear wave mode power which cannot be supplied from the power circuit 320 to the transmission circuit 330.

Since the high voltage power source 310 additionally supplies the insufficient power of the shear wave mode power to the transmission circuit 330, the power circuit 320 may supply the shear wave mode power to the transmission circuit 330 constantly. In other words, sum of a current supplied from the high voltage power source 310 and a current supplied from the capacitor 401 in the power circuit 320 is a current supplied to the transmission circuit 330, and the ultrasound diagnosis apparatus 300 may control operations of the power circuit 320 and the high voltage power source 310 such that the current supplied to the transmission circuit 330 is constant.

As illustrated in FIG. 6, a sum of a current ① supplied from the high voltage power source 310 to the transmission circuit 330 and a current ② supplied from the capacitor 401 in the power circuit 320 to the transmission circuit 330 may be a value of a final current ③ supplied to the transmission circuit 330. Referring to a graph of FIG. 6, the current ② supplied from the capacitor 401 in the power circuit 320 to the transmission circuit 330 may be calculated from a region generated from a difference between the final current ③ supplied to the transmission circuit 330 and the current ① supplied from the high voltage power source 310 to the transmission circuit 330. Since the shear wave mode power is stably, constantly supplied to the transmission circuit 330, a waveform 610 of a push pulse applied by the transmission circuit 330 to generate a shear wave may be obtained without distortion, and a waveform 620 of a measure pulse corresponding to the push pulse may be obtained without distortion.

Figure 7:
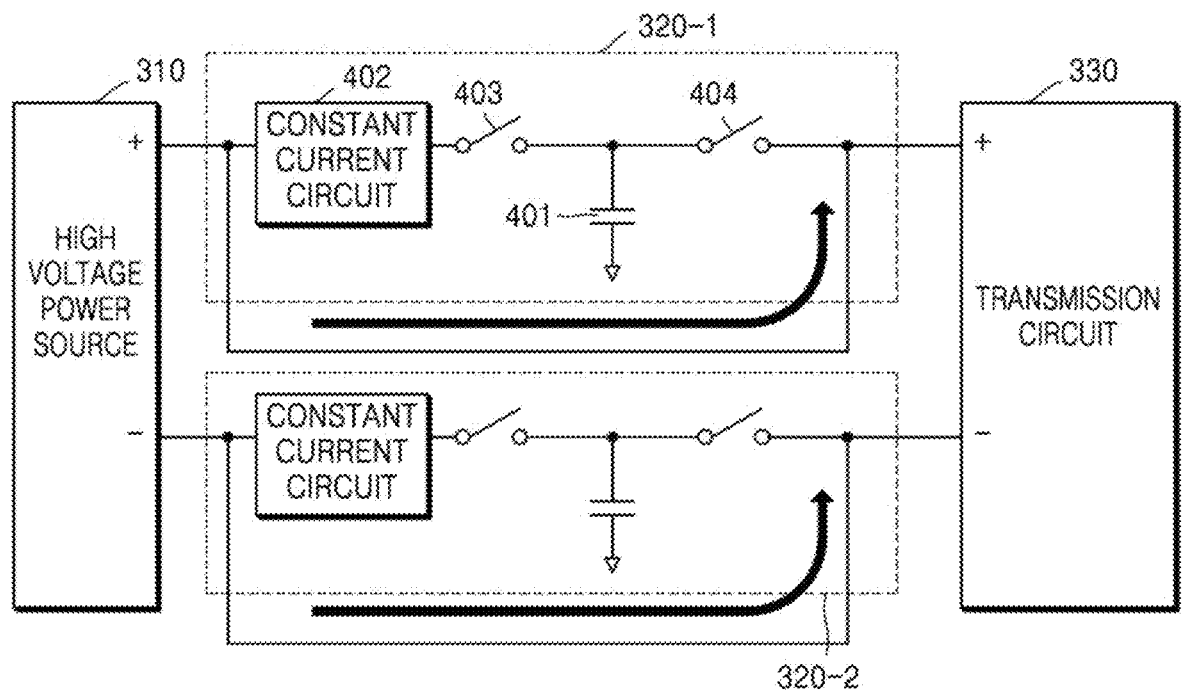
FIG. 7 is a view for explaining power supplied to a transmission circuit when an ultrasound diagnosis apparatus operates in a mode other than a shear wave mode, according to an embodiment.

FIG. 7 is a view for explaining power supplied to a transmission circuit when the ultrasound diagnosis apparatus 300 operates in a mode other than a shear wave mode according to an embodiment.

The ultrasound diagnosis apparatus 300 may obtain ultrasound images corresponding to operations of a plurality of modes. For example, the plurality of modes may include an amplitude (A) mode, a brightness (B) mode, a color (C) mode, a Doppler (D) mode, a motion (M) mode, and a shear wave mode, and it may be understood by those of ordinary skill in the art that other modes may be included.

For example, when the ultrasound diagnosis apparatus 300 operates in the B mode, the ultrasound diagnosis apparatus 300 may extract a B mode component from ultrasound data to generate an ultrasound image in which strength of a signal is expressed in terms of brightness. In contrast, when the ultrasound diagnosis apparatus 300 operates in the shear wave mode, the ultrasound diagnosis apparatus 300 may calculate a propagation velocity of a shear wave from ultrasound data to generate an elasticity image.

In the case where the ultrasound diagnosis apparatus 300 operates in the shear wave mode and in the case where the ultrasound diagnosis apparatus 300 operates in a mode other than the shear wave, since powers required by the transmission circuit 330 for a predetermined time are different from each other, the ultrasound diagnosis apparatus 300 may control an operation of the power circuit 320 depending on whether the shear wave mode is in operation.

Specifically, since a high voltage is required for a predetermined short time to generate a shear wave, when the ultrasound diagnosis apparatus 300 operates in the shear wave mode, the ultrasound diagnosis apparatus 300 may control an operation of the power circuit 320 such that electric energy stored in the power circuit 320 is supplied to the transmission circuit 330. In contrast, when the ultrasound diagnosis apparatus 300 operates in a mode other than the shear wave mode, the ultrasound diagnosis apparatus 300 may control an operation of the power circuit 320 such that the electric energy stored in the power circuit 320 is not supplied to the transmission circuit 330.

When the ultrasound diagnosis apparatus 300 operates in a mode other than the shear wave mode, as illustrated in FIG. 7, the ultrasound diagnosis apparatus 300 may supply required power to the transmission circuit 330 along a path in which the high voltage power source 310 is connected with the transmission circuit 330. The ultrasound diagnosis apparatus 300 may control the power circuit 320 such that the capacitor 401 is not charged with electric energy by turning off the first switch 403 of the power circuit 320. Also, the ultrasound diagnosis apparatus 300 may control the power circuit 320 such that electric energy with which the capacitor 401 is charged is not supplied to the transmission circuit 330 by turning off the second switch 404. That is, the ultrasound diagnosis apparatus 300 may control the power circuit 320 such that only the high voltage power source 310 supplies required power to the transmission circuit 330.

Figure 8:
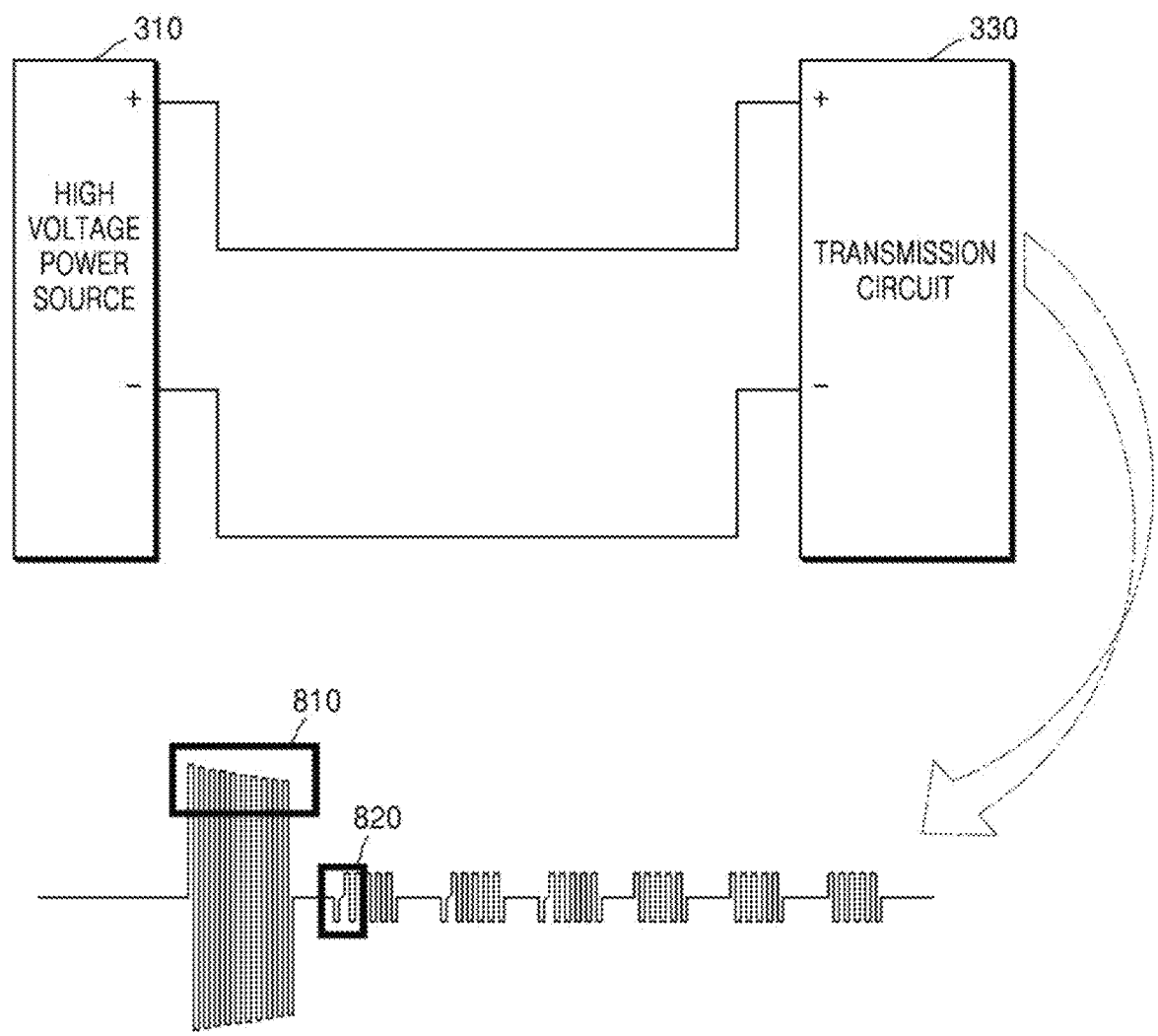
FIG. 8 is a view of a distorted pulse generated in an ultrasound diagnosis apparatus when the ultrasound diagnosis apparatus operates in a shear wave mode without a power circuit, according to an embodiment.

FIG. 8 is a view of a distorted pulse generated in the ultrasound diagnosis apparatus 300 when the ultrasound diagnosis apparatus operates in a shear wave mode without a power circuit according to an embodiment.

Referring to FIG. 8, the ultrasound diagnosis apparatus 300 does not include the power circuit 320 configured to supply shear wave mode power to the transmission circuit 330 when the shear wave mode is executed. When the ultrasound diagnosis apparatus 300 operates in the shear wave mode without the power circuit 320, the ultrasound diagnosis apparatus 300 generates a distorted pulse.

As illustrated in FIG. 8, the ultrasound diagnosis apparatus 300 may condense an ultrasound wave and generate a long burst Tx to generate a shear wave. However, when the long burst Tx is generated and an overload is generated to the high voltage power source 310 in the ultrasound diagnosis apparatus 300, distortion of a pulse waveform 810 of the long burst Tx may be generated. When distortion of the pulse waveform 810 is generated, the ultrasound diagnosis apparatus 300 may generate an abnormal shear wave, shear wave generation may not be properly performed, and distortion of the waveform may act as noises.

Also, as illustrated in FIG. 8, distortion of a measure waveform 820 may be generated when the pulse waveform 810 is generated and measure Tx is executed before a load in the ultrasound diagnosis apparatus 300 is restored to a normal state. Therefore, noises are generated to the measure waveform 820 measured by the ultrasound diagnosis apparatus 300, an operation speed of the ultrasound diagnosis apparatus 300 gets slow, and quality of an ultrasound image generated by the ultrasound diagnosis apparatus 300 is lowered. Due to the distorted waveform, the ultrasound diagnosis apparatus 300 cannot accurately diagnose an object. Therefore, the power circuit 320 for reducing a load of the high voltage power source 310 and generating a distortion-free pulse waveform for a long burst Tx is required.

Meanwhile, a circuit diagram shown in FIG. 8 may be substantially the same as the circuit diagram shown in FIG. 7 which operates in the ultrasound diagnosis apparatus 300 when the ultrasound diagnosis apparatus 300 operates in a mode other than the shear wave mode. Therefore, the circuit diagram shown in FIG. 8 may be a circuit diagram suitable for a case where the ultrasound diagnosis apparatus 300 operates in a mode other than the shear wave mode.

Figure 9:
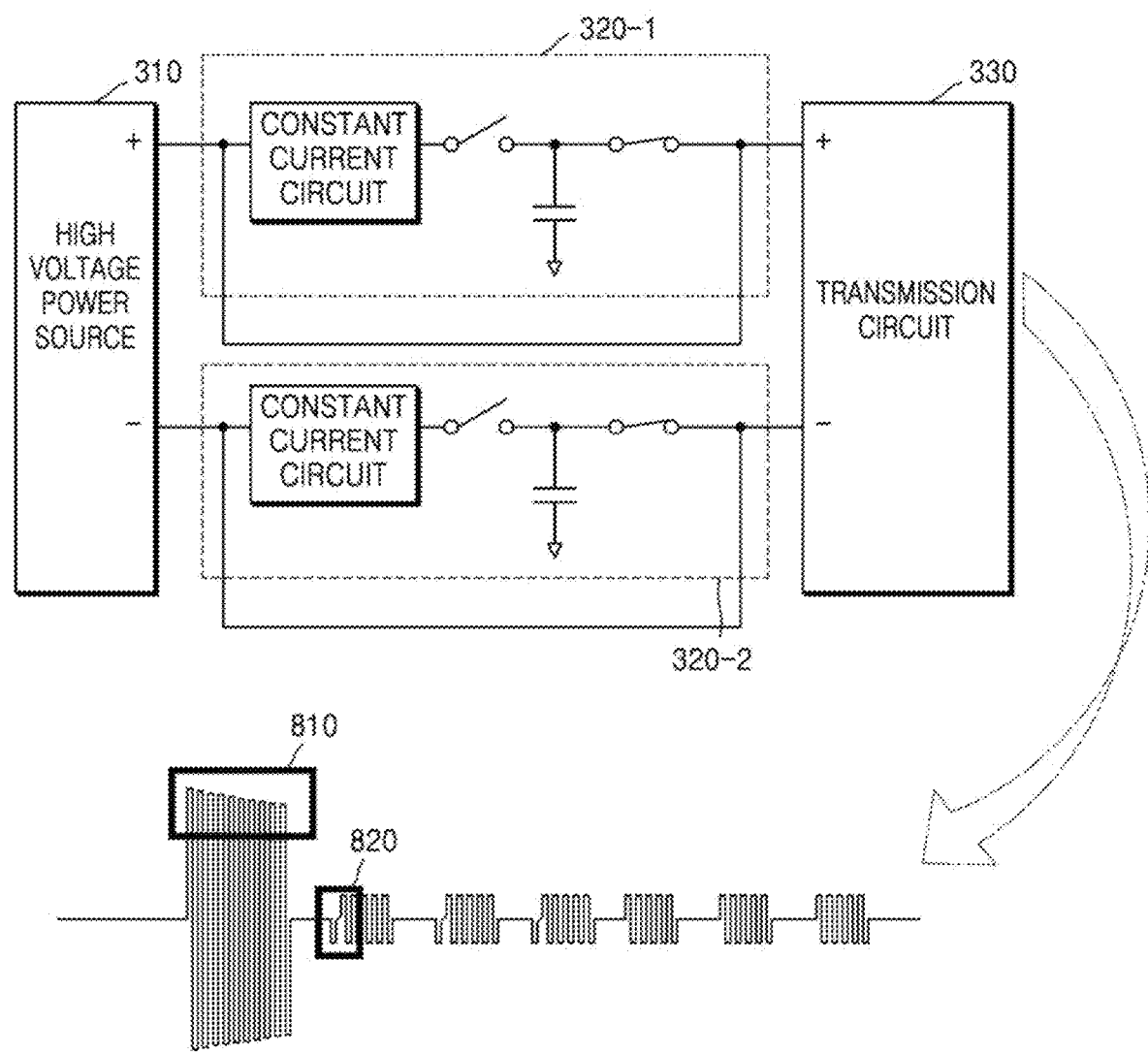
FIG. 9 is a view of a distortion-free pulse generated in an ultrasound diagnosis apparatus when the ultrasound diagnosis apparatus has a power circuit mounted thereon and operates in a shear wave mode, according to an embodiment.

FIG. 9 is a view of a distortion-free pulse generated in an ultrasound diagnosis apparatus when the ultrasound diagnosis apparatus 300 mounts a power circuit and operates in a shear wave mode according to an embodiment.

Referring to FIG. 9, the ultrasound diagnosis apparatus 300 includes the power circuit 320 configured to supply shear wave mode power to the transmission circuit 330 when the ultrasound diagnosis apparatus 300 operates in the shear wave mode. When the ultrasound diagnosis apparatus 300 operates in the shear wave mode, the ultrasound diagnosis apparatus 300 generates a distortion-free pulse.

Meanwhile, the power circuit 320 shown in FIG. 9 may be designed in a detachable form. Therefore, the circuit diagram of FIG. 8 may be complemented by additionally installing the power circuit 320 to the circuit diagram shown in FIG. 8. As illustrated in FIG. 9, the power circuit 320-1 may be connected and arranged between the (+) terminal of the high voltage power source 310 and the (+) terminal of the transmission circuit 330. Also, the power circuit 320-1 may be connected and arranged between the (−) terminal of the high voltage power source 310 and the (−) terminal of the transmission circuit 330.

As illustrated in FIG. 9, the ultrasound diagnosis apparatus 300 may condense an ultrasound wave and generate a long burst Tx to generate a shear wave. The ultrasound diagnosis apparatus 300 may reduce a load of the high voltage power source 310 by controlling the power circuit 320 such that shear wave mode power is supplied from the power circuit 320 to the transmission circuit 330. In this case, the ultrasound diagnosis apparatus 300 may control the high voltage power source 310 such that insufficient power of the shear wave mode power is supplied from the high voltage power source 310 to the transmission circuit 330.

Since the ultrasound diagnosis apparatus 300 controls the power circuit 320 and the high voltage power source 310 such that shear wave mode power is supplied constantly from the power circuit 320 to the transmission circuit 330, a pulse waveform 910 of a long burst Tx may be generated without distortion. Also, noises of another pulse 920 measured by the ultrasound diagnosis apparatus 300 are reduced, and the quality of an ultrasound image may improve.

Figure 10:
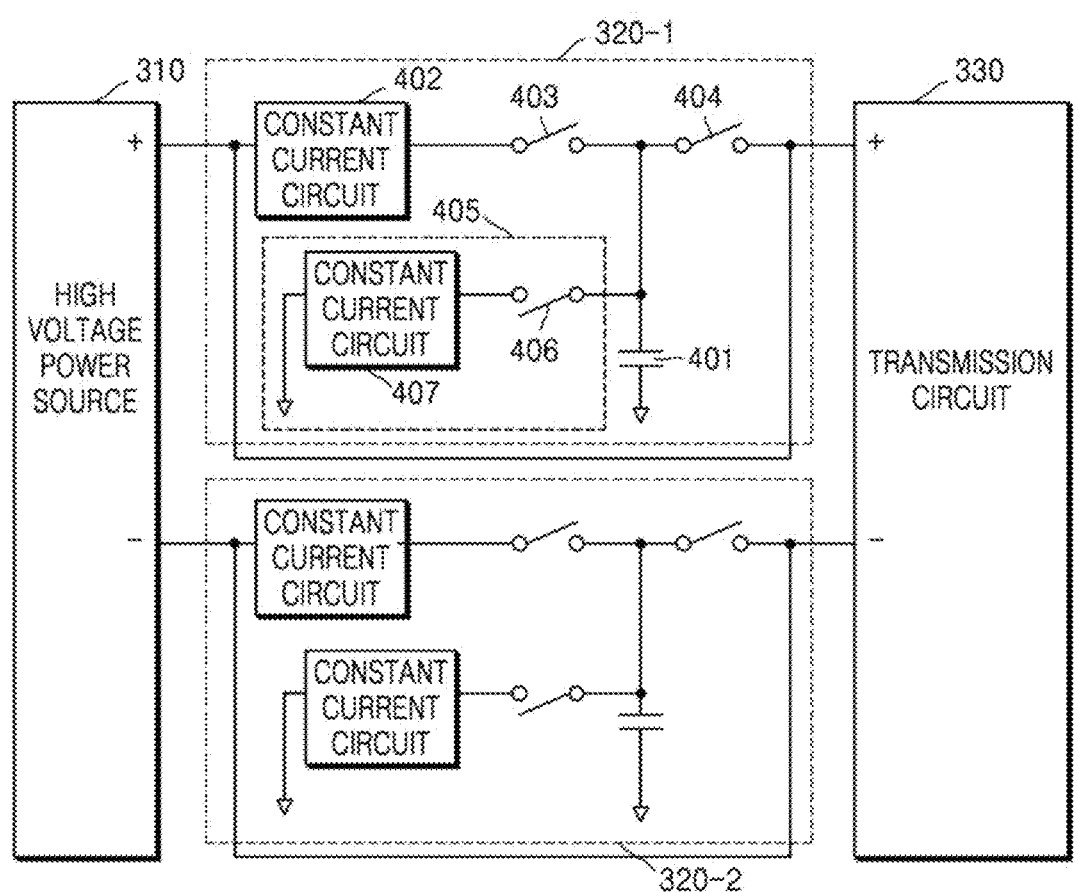
FIGS. 10 and 11 are views for explaining a process of discharging electric energy stored in a capacitor in a power circuit of an ultrasound diagnosis apparatus, according to an embodiment.
Figure 11:
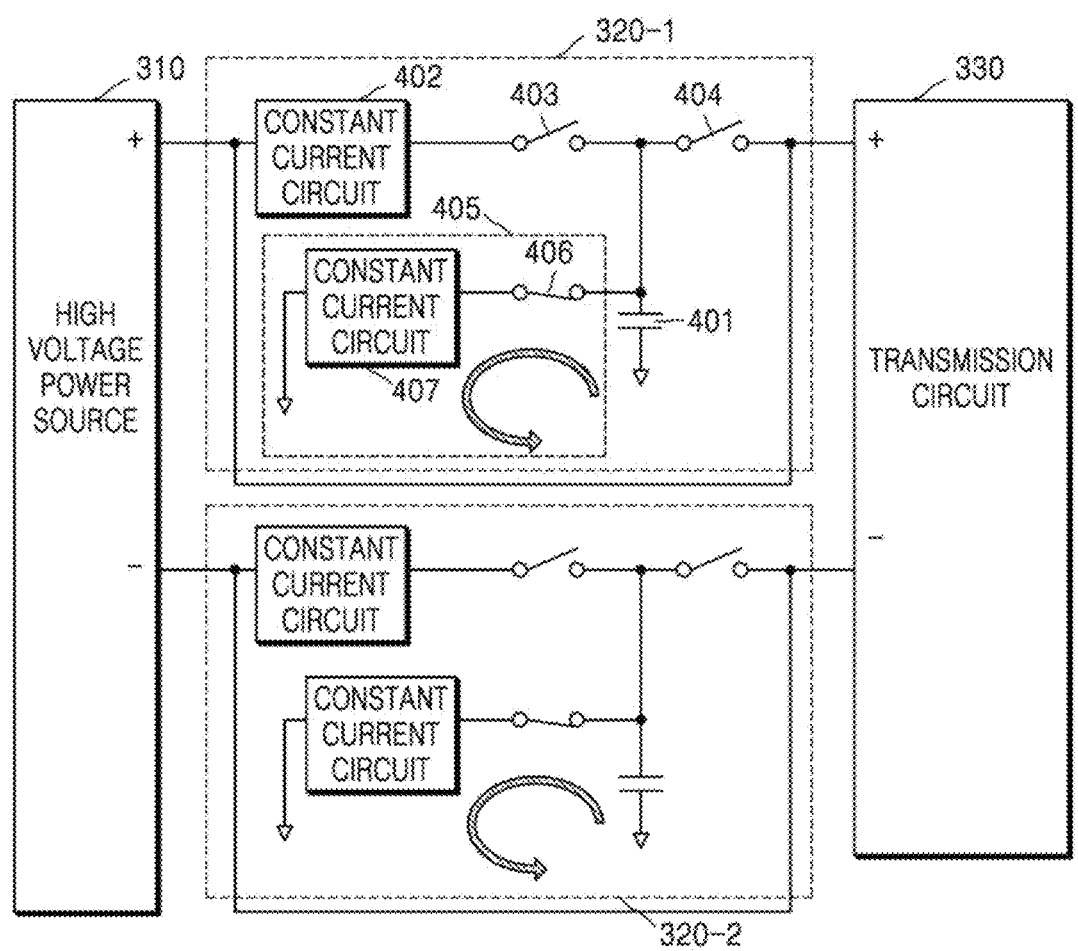

FIGS. 10 and 11 are views for explaining a process of discharging electric energy stored in the capacitor 401 in the power circuit 320 of the ultrasound diagnosis apparatus 300 according to an embodiment.

Referring to FIG. 10, in the case where electric energy with which the capacitor 401 in the power circuit 320 is charged is not discharged and is left consistently in the capacitor 401, a load may be applied consistently to the high voltage power source 310 of the ultrasound diagnosis apparatus 300, and a life of the capacitor 401 may be reduced. Therefore, the power circuit 320 of the ultrasound diagnosis apparatus 300 may further include a discharging circuit 405 configured to discharge the electric energy stored in the capacitor 401 in the power circuit 320. In the case where the ultrasound diagnosis apparatus 300 ends normally or ends abnormally, the ultrasound diagnosis apparatus 300 may discharge electric energy with which the capacitor 401 is charged through the discharging circuit 405. Also, when the ultrasound diagnosis apparatus 300 does not operate in the shear wave mode, the ultrasound diagnosis apparatus 300 may not charge the capacitor 401 with electric energy and discharge the electric energy left in the capacitor 401 through the discharging circuit 405.

The discharging circuit 405 may include a third switch 406 configured to control connection between the capacitor 401 and the ground. Also, the discharging circuit 405 may further include a constant current circuit 407 between the third switch 406 and the ground. The power circuit 320 including the discharging circuit 405 shown in FIG. 10 is only an example, and it will be understood by those of ordinary skill in the art that the discharging circuit 405 may include other elements besides the element shown in FIG. 10.

Also, as illustrated in FIG. 10, the third switch 406 configured to control the connection between the capacitor 401 and the ground may be connected with a node between the first switch 403 and the second switch 404.

Referring to FIG. 11, in the case where the shear wave mode ends or an operation of charging the capacitor 401 with electric energy is not performed, the ultrasound diagnosis apparatus 300 may discharge the electric energy with which the capacitor 401 is charged by controlling the discharging circuit 405 such that the capacitor 401 is connected with the ground by turning on the third switch 406. In this case, since the first switch 403 and the second switch 404 in the power circuit 320 are turned off, the capacitor 401 is not charged with electric energy and the electric energy with which the capacitor 401 is charged is not supplied to the transmission circuit 330. That is, electric energy left in the capacitor 401 may be discharged through the ground. Since the constant current circuit 407 in the discharging circuit 405 of the power circuit 320 is controlled such that a constant current flows from the capacitor 401 to the ground regardless of the electric energy left in the capacitor 401 or a value of a voltage applied to the capacitor 401, the electric energy left in the capacitor 401 may be discharged.

Figure 12:
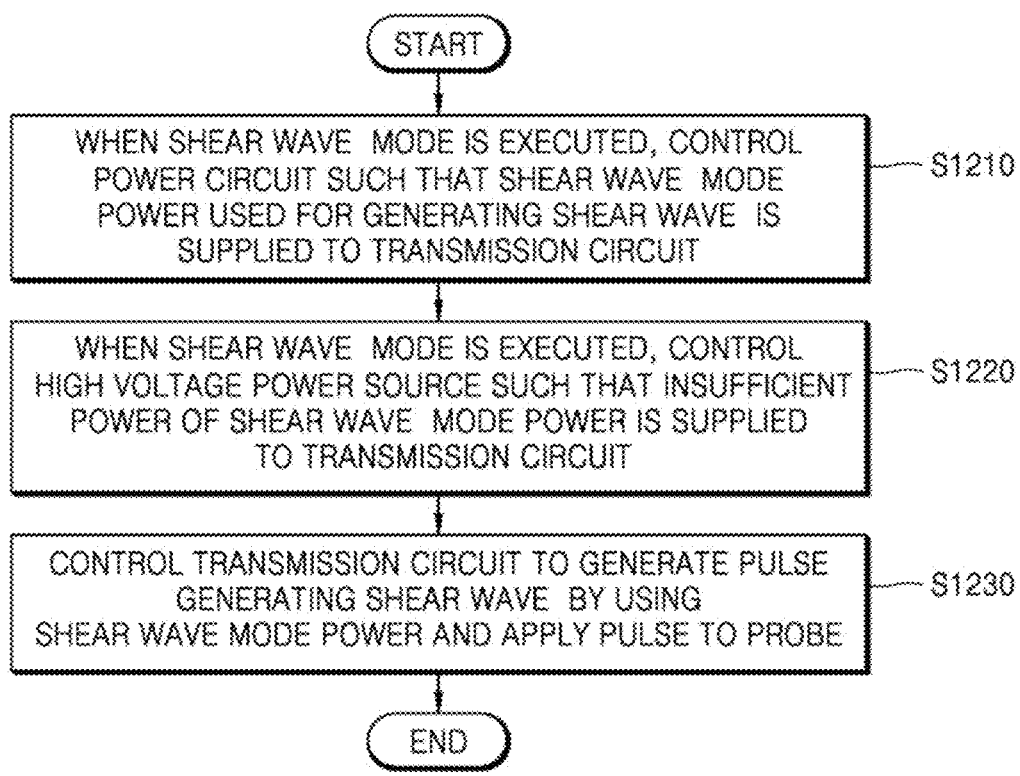
FIG. 12 is a flowchart for explaining a method of operating an ultrasound diagnosis apparatus which generates a shear wave, according to an embodiment.

FIG. 12 is a flowchart for explaining a method of operating the ultrasound diagnosis apparatus 300 which generates a shear wave according to an embodiment.

In operation S1210, when the ultrasound diagnosis apparatus 300 operates in a shear wave mode, the ultrasound diagnosis apparatus 300 may control the power circuit 320 in the ultrasound diagnosis apparatus 300 such that shear wave mode power used for generating a shear wave is supplied to the transmission circuit 330.

Specifically, the ultrasound diagnosis apparatus 300 may control the power circuit 320 such that the capacitor 401 is charged with power supplied from the high voltage power source 310 in the ultrasound diagnosis apparatus 300 as electric energy. The ultrasound diagnosis apparatus 300 may control the power circuit 320 such that shear wave mode power is supplied to the transmission circuit 330 in the ultrasound diagnosis apparatus 300 based on the electric energy with which the capacitor 401 is charged.

In operation S1220, the ultrasound diagnosis apparatus 300 may control the high voltage power source 310 such that insufficient power of the shear wave mode power is supplied to the transmission circuit 330. Specifically, when the shear wave mode power is supplied from the power circuit 320 to the transmission circuit 330, the electric energy with which the power circuit 320 is charged may be reduced. When the electric energy with which the power circuit 320 is charged is reduced, the ultrasound diagnosis apparatus 300 may control the high voltage power source 310 such that a magnitude of insufficient power of the shear wave mode power increases as much as a magnitude by which the shear wave mode power supplied from the power circuit 320 to the transmission circuit 330 is reduced. That is, the ultrasound diagnosis apparatus 300 may control supplying of the shear wave mode power such that electric energy reduced in the capacitor is complemented by controlling the power circuit 320 and the high voltage power source 310. The ultrasound diagnosis apparatus 300 may control the power circuit 320 and the high voltage power source 310 such that the shear wave mode power is supplied constantly from the power circuit 320 to the transmission circuit 330.

In operation S1230, the ultrasound diagnosis apparatus 300 may control the transmission circuit 330 to generate a pulse for generating a shear wave by using the shear wave mode power. The ultrasound diagnosis apparatus 300 may control the transmission circuit 330 to apply the generated pulse to a probe in the ultrasound diagnosis apparatus 300. The ultrasound diagnosis apparatus 300 may control the probe to transmit a shear wave to an object. The ultrasound diagnosis apparatus 300 may generate an elasticity image by receiving an echo signal of a shear wave reflected from the object and calculating a propagation velocity of the shear wave.

Figure 13:
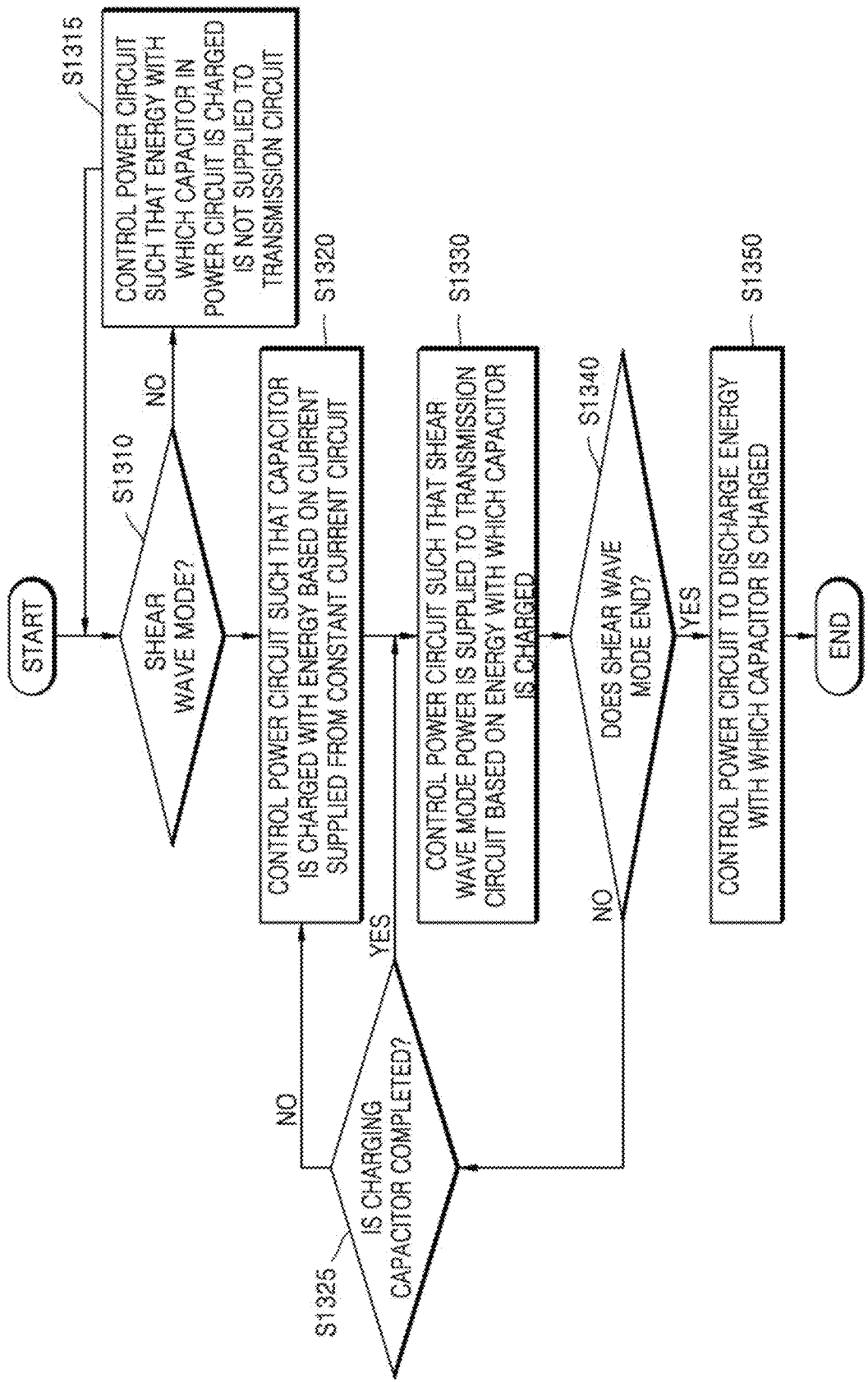
FIG. 13 is a flowchart for explaining a method of operating an ultrasound diagnosis apparatus which generates a shear wave, according to another embodiment.

FIG. 13 is a flowchart for explaining a method of operating the ultrasound diagnosis apparatus 300 which generates a shear wave according to another embodiment.

In operation S1310, the ultrasound diagnosis apparatus 300 may determine an operation mode for generating an ultrasound wave. When an operation mode of the ultrasound diagnosis apparatus 300 is a shear wave mode, the ultrasound diagnosis apparatus 300 may perform an operation according to operation S1320. In contrast, when an operation mode of the ultrasound diagnosis apparatus 300 is not the shear wave mode, the ultrasound diagnosis apparatus 300 may perform an operation according to operation S1315.

In operation S1315, the ultrasound diagnosis apparatus 300 may control the power circuit 320 such that electric energy with which the capacitor 401 in the power circuit 320 is charged is not supplied to the transmission circuit 330. Specifically, the ultrasound diagnosis apparatus 300 may block an operation of the power circuit 320 such that the electric energy with which the capacitor 401 in the power circuit 320 is charged is not supplied to the transmission circuit 330. Also, in the case where the capacitor 401 in the power circuit 320 is not charged with electric energy, the ultrasound diagnosis apparatus 300 may control the power circuit 320 such that shear wave mode power is not supplied to the transmission circuit 330 through the power circuit 320.

Also, in operation S1315, the ultrasound diagnosis apparatus 300 may control the power circuit 320 such that the capacitor 401 in the power circuit 320 is not charged with electric energy.

In operation S1320, the ultrasound diagnosis apparatus 300 may control an operation of a device in the power circuit 320 such that the power circuit 320 is charged with electric energy. For example, the power circuit 320 may include a capacitor, a constant current circuit, a first switch, and a second switch. The capacitor may be charged with electric energy for supplying shear wave mode power. The constant current circuit may supply electric energy for supplying the shear wave mode power to the capacitor. The first switch may control connection between the constant current circuit and the capacitor. The second switch may control connection between the capacitor and the transmission circuit 330. The ultrasound diagnosis apparatus 300 may charge the capacitor with electric energy by controlling the power circuit 320 such that the constant current circuit is connected with the capacitor by turning on the first switch and connection between the capacitor and the transmission circuit 330 is cut off by turning off the second switch.

In operation S1325, the ultrasound diagnosis apparatus 300 may determine whether the charging of the capacitor in the power circuit 320 with electric energy is completed. When the charging of the capacitor with electric energy is completed, the ultrasound diagnosis apparatus 300 may perform an operation according to operation S1330. In contrast, when the charging of the capacitor with electric energy is not completed, the ultrasound diagnosis apparatus 300 may perform an operation according to operation S1320.

In operation S1330, the ultrasound diagnosis apparatus 300 may control the power circuit 320 such that shear wave mode power is supplied to the transmission circuit 330 based on the electric energy with which the power circuit 320 is charged. For example, the ultrasound diagnosis apparatus 300 may supply the shear wave mode power to the transmission circuit 330 by controlling the power circuit 320 such that connection between the constant current circuit and the capacitor is cut off by turning off the first switch and the capacitor is connected with the transmission circuit 330 by turning on the second switch. That is, the ultrasound diagnosis apparatus 300 may control the first switch and the second switch such that the shear wave mode power is supplied to the transmission circuit 330 based on the electric energy with which the capacitor in the power circuit 320 is charged.

In operation S1340, the ultrasound diagnosis apparatus 300 may determine whether the shear wave mode of the ultrasound diagnosis apparatus 300 has ended. Also, the ultrasound diagnosis apparatus 300 may determine whether an operation of charging the power circuit 320 with electric energy is not performed. When the shear wave mode of the ultrasound diagnosis apparatus 300 has ended and the operation of charging the power circuit 320 with electric energy is not performed, the ultrasound diagnosis apparatus 300 may perform an operation according to operation S1350. Also, when the shear wave mode of the ultrasound diagnosis apparatus 300 has ended and the operation of charging the power circuit 320 with electric energy is not performed, the ultrasound diagnosis apparatus 300 may also perform an operation according to operation S1325.

In operation S1350, the ultrasound diagnosis apparatus 300 may control the power circuit 320 to discharge electric energy with which the power circuit 320 is charged. For example, the power circuit 320 may further include a discharging circuit configured to discharge the electric energy with which the capacitor in the power circuit 320 is charged. The discharging circuit may include a third switch configured to control connection between the capacitor and the ground. The ultrasound diagnosis apparatus 300 may control the discharging circuit such that the electric energy with which the capacitor is charged is discharged by turning on the third switch and thus connecting the capacitor with the ground. That is, the ultrasound diagnosis apparatus 300 may control an operation of the third switch to discharge remaining electric energy after the power circuit 320 supplies the shear wave mode power to the transmission circuit 330.

The above-described ultrasound diagnosis apparatus 300 may be implemented as a hardware element, a software element, and/or a combination of a hardware element and a software element. For example, the apparatus and the elements described in the embodiments may be implemented by using, for example, a processor, a controller, arithmetic logic unit (ALU), a digital signal processor, a microcomputer, a field programmable array (FPA), a programmable logic unit (PLU), a microprocessor, and one or more general-purpose computers or specific-purpose computers such as any apparatus that may execute an instruction and respond thereto.

The processor may perform an operating system (OS) and one or more software applications performed on the OS. Also, the processor may access, store, manipulate, process, and generate data in response to execution of software.

For convenience of understanding, though one processor is used in the description, it will be understood by those of ordinary skill in the art that the processor may include a plurality of processing elements and/or a processing element having a plural form. For example, the processor may include a plurality of processors or one processor and one controller. Also, a different processing configuration such as a parallel processor may be used.

Software may include a computer program, a code, an instruction, or a combination of one or more of these, and configure a processor to operate in a desired fashion, or command the processor independently or collectively.

Software and/or data may be embodied in a certain type of machine, a component, a physical apparatus, virtual equipment, a computer storage medium or device, or a transmitted signal wave permanently or temporarily such that the software and/or data are analyzed by the processor or to provide an instruction or data to the processor. Software may be distributed over network coupled computer systems so that the software is stored and executed in a distributive manner. Software and data may be stored in one or more non-transitory computer-readable recording media.

The method according to the embodiments may be implemented in the form of a program instruction executable through various computer means and recorded on a computer-readable recording medium. The computer-readable recording medium may include a program instruction, a data file, a data structure, etc. in a single form or a combination thereof. The program instructions recorded in the computer-readable recording medium may be things particularly designed and configured for the embodiments, or things known to and available in computer software programmers. Examples of the non-transitory computer-readable recording medium include magnetic recording media such as hard disks, floppy disks, and magnetic tapes, optical recording media such as CD-ROMs and DVDs, magneto-optical recording media such as floptical disks, and hardware devices such as ROMs, RAMs, and flash memories that are especially configured to store and execute program instructions.

Examples of the program instructions include machine language codes that may be generated by a compiler, and high-level language codes that may be executed by a computer by using an interpreter.

The hardware apparatus may be configured as one or more software modules for performing operations of the embodiments, and vice versa.

Though the embodiments have been described with reference to limited embodiments and drawings, it will be obvious to those of ordinary skill in the art that various modifications and changes may be made from the above descriptions. For example, the described technologies may be performed in a sequence different from those of the described methods, and/or the elements such as the described system, structure, apparatus, and circuit may be coupled or combined in a form different from the described methods, or a proper result may be accomplished even though the elements are replaced with other elements or equivalents thereof.

Therefore, the scope of the present disclosure should not be limited to the described embodiments and should be defined by the following claims and equivalents thereof.

What is claimed is:

1. An ultrasound diagnosis apparatus comprising:
a high voltage power source;
a transmission circuit configured to receive power from the high voltage power source, generate a pulse generating an ultrasound wave, and apply the ultrasound wave to a probe in the ultrasound diagnosis apparatus;
a power circuit configured to receive the power from the high voltage power source and be charged with electric energy when the ultrasound diagnosis apparatus operates in a shear wave mode, and supply, to the transmission circuit, shear wave mode power used for generating a shear wave, based on the electric energy; and
a processor configured to control the power circuit configured to supply the shear wave mode power when the shear wave mode is in operation,
wherein the processor is further configured to control the high voltage power source and the power circuit such that insufficient power of the shear wave mode power is supplied from the high voltage power source to the transmission circuit and the shear wave mode power is constantly supplied to the transmission circuit to prevent distortion of a pulse for generating the shear wave.

2. The ultrasound diagnosis apparatus of claim 1, wherein when the electric energy stored in the power circuit is reduced when the shear wave mode power is supplied from the power circuit to the transmission circuit, the processor is further configured to control the high voltage power source and the power circuit such that the insufficient power supplied from the high voltage power source increases.

3. The ultrasound diagnosis apparatus of claim 1, wherein the power circuit comprises:
a capacitor charged with the electric energy for supplying the shear wave mode power;
a constant current circuit connected with the high voltage power source, and configured to supply the electric energy for supplying the shear wave mode power to the capacitor;
a first switch configured to control a connection between the constant current circuit and the capacitor; and
a second switch configured to control a connection between the capacitor and the transmission circuit.

4. The ultrasound diagnosis apparatus of claim 3, wherein the processor is further configured to control the power circuit such that the connection between the constant current circuit and the capacitor is cut off by turning off the first switch, and the capacitor is connected with the transmission circuit by turning on the second switch, to supply the shear wave mode power to the transmission circuit based on the electric energy stored in the capacitor.

5. The ultrasound diagnosis apparatus of claim 3, wherein the processor is further configured to control the power circuit such that the constant current circuit is connected with the capacitor by turning on the first switch, and the connection between the capacitor and the transmission circuit is cut off by turning off the second switch, to charge the capacitor with the electric energy based on a current supplied from the constant current circuit.

6. The ultrasound diagnosis apparatus of claim 3, wherein the power circuit further comprises a discharging circuit configured to discharge the electric energy stored in the capacitor.

7. The ultrasound diagnosis apparatus of claim 6, wherein the discharging circuit comprises a third switch configured to control a connection between the capacitor and a ground, and when the shear wave mode ends or an operation of charging the capacitor with the electric energy is not performed, the processor is further configured to control the discharging circuit such that the capacitor is connected with the ground by turning on the third switch to discharge the electric energy stored in the capacitor.

8. The ultrasound diagnosis apparatus of claim 1, wherein the transmission circuit is further configured to generate the pulse for generating the shear wave by using the shear wave mode power and applies the pulse to the probe.

9. The ultrasound diagnosis apparatus of claim 8, wherein the processor is further configured to control the probe such that the shear wave is transmitted to an object, an echo signal of the shear wave, reflected from the object, is received to calculate a propagation velocity of the shear wave, and an elasticity image is generated.

10. The ultrasound diagnosis apparatus of claim 1, wherein the processor is further configured to control the power circuit such that the electric energy stored in the power circuit is supplied to the transmission circuit when the shear wave mode is in operation, and control the power circuit such that the electric energy stored in the power circuit is not supplied to the transmission circuit when a mode other than the shear wave mode is in operation.

11. A method of operating an ultrasound diagnosis apparatus for generating a shear wave, the method comprising:
controlling a power circuit in the ultrasound diagnosis apparatus such that power supplied from a high voltage power source in the ultrasound diagnosis apparatus is stored as electric energy when the ultrasound diagnosis apparatus operates in a shear wave mode, and shear wave mode power used for generating the shear wave is supplied to a transmission circuit in the ultrasound diagnosis apparatus, based on the electric energy;
controlling the high voltage power source and the power circuit such that insufficient power of the shear wave mode power is supplied to the transmission circuit when the shear wave mode is in operation and the shear wave mode power is constantly supplied to the transmission circuit to prevent distortion of a pulse for generating the shear wave; and
controlling the transmission circuit to generate the pulse for generating the shear wave by using the shear wave mode power, and apply the pulse to a probe in the ultrasound diagnosis apparatus.

12. The method of claim 11, wherein the controlling of the high voltage power source such that the insufficient power of the shear wave mode power is supplied to the transmission circuit comprises:
controlling the high voltage power source and the power circuit such that when the electric energy stored in the power circuit is reduced when the shear wave mode power is supplied from the power circuit to the transmission circuit, the insufficient power supplied from the high voltage power source increases.

13. The method of claim 11, wherein the power circuit comprises:
a capacitor to charge the electric energy for supplying the shear wave mode power;
a constant current circuit connected with the high voltage power source, and configured to supply the electric energy for supplying the shear wave mode power to the capacitor;
a first switch configured to control a connection between the constant current circuit and the capacitor; and
a second switch configured to control a connection between the capacitor and the transmission circuit.

14. The method of claim 13, wherein the controlling of the power circuit such that the shear wave mode power is supplied to the transmission circuit comprises:
controlling the power circuit such that the connection between the constant current circuit and the capacitor is cut off by turning off the first switch, and the capacitor is connected with the transmission circuit by turning on the second switch.

15. The method of claim 13, wherein the controlling of the power circuit such that the shear wave mode power is supplied to the transmission circuit comprises: controlling the power circuit such that the capacitor is charged with the electric energy.

16. The method of claim 15, wherein the controlling of the power circuit such that the capacitor is charged with the electric energy comprises: controlling the power circuit such that the constant current circuit is connected with the capacitor by turning on the first switch, and the connection between the capacitor and the transmission circuit is cut off by turning off the second switch.

17. The method of claim 13, wherein the power circuit further comprises a discharging circuit configured to discharge the electric energy with which the capacitor is charged, the discharging circuit comprising a third switch configured to control a connection between the capacitor and a ground, and
the method further comprises, when the shear wave mode ends or an operation of charging the capacitor with the electric energy is not performed, controlling the discharging circuit to discharge the electric energy with which the capacitor is charged by turning on the third switch and thus connecting the capacitor with the ground.

18. The method of claim 11, further comprising:
controlling the probe to transmit the shear wave to an object; and
generating an elasticity image by receiving an echo signal of the shear wave reflected from the object and calculating a propagation velocity of the shear wave.

19. The method of claim 11, wherein the controlling of the power circuit such that the shear wave mode power is supplied to the transmission circuit comprises:
when the shear wave mode is in operation, controlling the power circuit such that the electric energy with which the power circuit is charged is supplied to the transmission circuit; and
when a mode other than the shear wave mode is in operation, controlling the power circuit such that the electric energy with which the power circuit is charged is not supplied to the transmission circuit.

20. A non-transitory computer-readable recording medium having recorded thereon a program for executing a method of operating an ultrasound diagnosis apparatus for generating a shear wave, the method comprising:
controlling a power circuit in the ultrasound diagnosis apparatus such that power supplied from a high voltage power source in the ultrasound diagnosis apparatus is stored as electric energy when the ultrasound diagnosis apparatus operates in a shear wave mode, and shear wave mode power used for generating the shear wave is supplied to a transmission circuit in the ultrasound diagnosis apparatus, based on the electric energy;

controlling the high voltage power source and the power circuit such that insufficient power of the shear wave mode power is supplied to the transmission circuit when the shear wave mode is in operation and the shear wave mode power is constantly supplied to the transmission circuit to prevent distortion of a pulse for generating the shear wave; and controlling the transmission circuit to generate the pulse for generating the shear wave by using the shear wave mode power, and apply the pulse to a probe in the ultrasound diagnosis apparatus.

\* \* \* \* \*